United States Patent [19]

Morgenthaler

[11] Patent Number: 4,934,365

[45] Date of Patent: Jun. 19, 1990

[54] NON-INVASIVE HYPERTHERMIA METHOD AND APPARATUS

[75] Inventor: Frederic R. Morgenthaler, Wellesley Hills, Mass.

[73] Assignee: Massachusetts Institute of Technology, Cambridge, Mass.

[21] Appl. No.: 213,736

[22] Filed: Jun. 30, 1988

[51] Int. Cl.$^5$ .............................................. A61N 5/00
[52] U.S. Cl. ..................................... 128/399; 128/304
[58] Field of Search ............. 128/804, 399, 422, 24 A

[56] References Cited

U.S. PATENT DOCUMENTS

| 4,646,756 | 3/1987 | Watmough et al. | 128/804 |
| 4,672,980 | 6/1987 | Turner | 128/804 |
| 4,700,716 | 10/1987 | Kasevich et al. | 128/804 |
| 4,702,262 | 10/1987 | Anderson et al. | 128/804 |

FOREIGN PATENT DOCUMENTS

| 2420888 | 11/1975 | Fed. Rep. of Germany | 128/804 |
| 1045546 | 10/1966 | United Kingdom | 128/804 |
| WO88/03823 | 6/1988 | World Int. Prop. O. | |

OTHER PUBLICATIONS

Gerner et al, "The Potential . . . Therapy", Radiology, 116:433-439, Aug. 1975.
"Localized Hyperthermia with Electromagnetic Arrays and the Leaky-Wave Troughguide Applicator", Rappaport et al., No. 2(1971), *IEEE Transactions on Microwave Theory and Techniques*, vol. MTT-19.
"Analyses of Electromagnetic Fields Induced in Biological Tissues by Thermographic Studies on Equivalent Phantom Models", Arthur W. Guy, *IEEE Transactions on Microwave Theory and Techniques*, vol. MTT-19, No. 2, Feb. 1971.
"Discussion of Capabilities of Microwave Phased Arrays for Hyperthermia Treatment of Neck Tumors", Jouvie et al., *IEEE Transactions on Microwave Theory and Techniques*, vol. MTT-34, No. 5, May 1986.
"Analysis of the Radiation Leakage for a Four-Aperture Phased-Array Applicator in Hyperthermia Therapy", Wait, James R., *IEEE Transactions on Microwave Theory and Techniques*, vol. MTT-34, No. 5, May 1986.
"Hyperthermia and Inhomogeneous Tissue Effects Using an Annular Phased Array", Turner, Paul F., *IEEE Transactions on Microwave Theory and Techniques*, vol. MTT-32, No. 8, Aug. 1984.
"Two-Dimensional Technique to Calculate the EM Power Deposition Pattern in the Human Body", Iskander et al., *Journal of Microwave Power*, 17(3), 1982.
"Focused Array Hyperthermia Applicator: Theory and Experiment", Gee et al., *IEEE Transactions on Biomedical Engineering*, vol. BME-31, No. 1, Jan. 1984.
"Experimental Study of the Controllable Microwave Troughguide Applicator", Rappaport et al., *J. Microwave Power*, 1987.
"Metallic Delay Lenses", Kock, Winston E., *Bell System Technical Journal*, vol. 27, 1948.
"An Electric Field Converging Applicator with Heating Pattern Controller for Microwave Hyperthermia", Nikawa et al., *IEEE Transactions on Microwave Theory and Techniques*, vol. MTT-34, No. 5, May 1986.
"Velocity Modulation of Electromagnetic Waves", Morgenthaler, F. C., Thesis, Massachusetts Institute of Technology, Jun. 1956.
"Synthesis of Optimum Microwave Antenna Applicators for Use in Treating Deep Localized Tumors", Rappaport, C. M., Thesis, Massachusetts Institute of Technology, Jun. 1987.
"The Clausius-Mossotti Problem for Cubic Arrays of Spheres", Doyle, W. T., *J. Appl. Phys.*, 49(2), Feb. 1978.

*Primary Examiner*—Lee S. Cohen
*Attorney, Agent, or Firm*—Hamilton, Brook, Smith & Reynolds

[57] ABSTRACT

A method and apparatus for non-invasive hyperthermia is described employing an electromagnetic (EM) energy generating applicator which utilizes in one embodiment an artificially simulated impedance matching layer for coupling energy to tissue. In another embodiment, the matching layer is comprised of varactor diodes and is voltage controllable. In another embodiment, the applicator utilizes a voltage controllable trough-guide applicator and, lastly, a combination ultrasound and EM applicator is described.

14 Claims, 9 Drawing Sheets

NON-INVASIVE HYPERTHERMIA METHOD AND APPARATUS

The Government has rights in this invention pursuant to Grant Number NIH-1-P01-CA31303 awarded by the National Institutes of Health.

BACKGROUND ART

Hyperthermia, or the use of elevated temperatures to repress tumors, has been known and studied for many years.

Many cancerous tumors embedded in healthy human tissue have well-defined boundaries and tend to be irreversibly damaged by hyperthermia. Tumor temperature elevation to 43°-46° C. for 90 to 120 minutes appears to be sufficient to kill many types of malignant growths. Several systems for generating and delivering heat to these localized tumors have been proposed. They include capacitive and inductive RF systems, use of a single microwave source, focused ultrasound systems, invasive electromagnetic probes, and microwave heating arrays. Much of the current interest is directed to non-invasive sources, which are less traumatic to sick patients and minimize the risk of mixing abnormal cells into healthy tissue.

External applicators are also more flexible than invasive ones It is possible for many of these applicators to be reconfigured to suit the requirements of a particular case. Also, a non-invasive applicator can be designed to surround the body part containing the tumor, taking advantage of constructive interference and focussing to concentrate more heat at the tumor than in the surrounding normal tissue.

The two broad classes of external hyperthermia applicators are electromagnetic (EM) and ultrasound (US). Electromagnetic applicators radiate waves which propagate at the speed of light, 300,000 km/sec in vacuum, or slower in matter, and are characterized by both a propagation direction, and a vector polarization. Ultrasound is an acoustic wave which cannot propagate in a vacuum, has a much slower velocity (about 1500 m/sec in soft biological tissue), and; since it is a compressional wave, does not have a polarization attribute.

As a wave propagates through a dissipative (lossy) medium, it attenuates as it deposits power, in the form of heat, in the medium. The attenuation rate is exponential, represented by $e^{-\alpha x}$, where x is depth into the medium and $\alpha$ is the attenuation rate. Since the attenuation rate varies directly with frequency, radiation at higher frequency penetrates less deeply than a lower frequency.

The spatially oscillatory nature of waves is described by the relation $\cos\beta x$, where $\beta = 2\pi/\lambda$ is the propagation constant, inversely proportional to wavelength. Any spatial features, such as peaks or troughs, will extend for a distance on the order of a wavelength. A major distinction between EM and US radiation is the much greater resolution and focussing ability of the latter. Since US propagation velocity is 200,000 times slower than that of EM, the propagation constant $\beta$ is much bigger for a given attenuation constant $\alpha$.

The entire spatial behavior of either type of wave is governed by the $\alpha$ and $\beta$ parameters. A convenient representation in terms of the complex wave number is:

$$k = \beta - j\alpha$$

The optimal non-invasive applicator delivers maximum power to the tumor while minimally heating surrounding healthy tissue. Since waves attenuate as they penetrate lossy tissue, a focussing source arrangement is required. Constructive interference at the tumor is obtained by adjusting the phase and amplitude of each point of the source. Unlike in free space, nearfield focussing in a lossy medium is more involved than simply compensating for the path length variations from tumor to source. Also, since the attenuation rate varies directly (though non-linearly) with frequency, while field resolution decreases with decreasing frequency, any attainable "focus" is relatively wide and of low intensity. The broadening and smearing of this focal maximum increases as the physical distance in the medium to the source increases, until the exponential decay overwhelms any geometrical focussing advantages. For heating a tumor in the center of a volume of tissue, the best range of frequencies is found by choosing those patterns of dissipated power (if any exist) that have the same or greater power at the focus as at the tissue surface with lower power for all intervening tissue, including muscle/fat boundaries. Generally, the sharpest focus or highest resolution will correspond to the highest possible frequency within this range of frequencies. Exceeding this range may produce higher resolution, but the actual penetration depth into the tissue will decrease.

More complicated than frequency selection is the determination of optimal source distribution. Unlike with the acoustic compression waves of ultrasound hyperthermia, electromagnetic waves incorporate polarization. For constructive interference at a focus, electric field at the tissue surface must be properly aligned and phased so that waves propagating along all paths in the entire tissue volume arrive in the same fashion. However, merely adjusting phase, polarization, and also amplitude for maximum focussing does not necessarily produce an acceptable power-density distribution.

Several experimental means of determining source distribution have been proposed. These include passive distribution methods, such as remote sensing and active methods, such as invasive implantation of a small source at the intended focus and subsequent phase measurement at the surface and inversion for source specification. Both methods overlook the difficulty of undesirable hot spots or excessive surface heating. Correcting the source distributions to prevent this often eliminates any geometrical advantage at the focus.

One further requirement of applicators is a method of monitoring power deposited in the exposed tissue. Applied dosage information may be used as an approximate substitute for the difficult problem of direct non-invasive temperature measurement.

Although the effects of phase focussing a wave in tissue is not as great as in free space, advantage can be taken of a finite tissue volume by surrounding it with applicator sources. Two main simplified cases that yield good power patterns have been examined. (See Rappaport, Cary M. and Morgenthaler F. R., "Localized Hyperthermia with Electromagnetic Arrays and the Leaky-Wave Troughguide Applicator", *IEEE Transactions on Microwave Theory and Techniques*, Vol. MTT-34, No. 5, May 1986.) The first case is that of planar arrays facing each other and the second case involves cylindrical arrays. In the above-referenced article, a troughguide leaky-wave antenna hyperthermia applicator was described which can be configured as either a planar array source or cylindrical array.

A leaky-wave antenna guides a controlled amount of power down its length. Boundary conditions for the interior propagating guided field at the opening are satisfied by a tangential E-field. Since the interior guided field propagates down the guide, the tangential E-field across the opening must have progressive linear phase. Thus, a non-uniform plane wave radiates at the angle θ from broadside specified by $$\theta = \sin^{-1}(\lambda_o/\lambda_g)$$

where $\lambda_o$ and $\lambda_g$ are the free-space and guide wavelengths, respectively.

The asymmetric troughguide is a leaky-wave antenna consisting of a U-shaped channel, open at one side, with a center fin attached to its base and running down its length. The base on one side of the central fin is raised, introducing the asymmetry that generates a tangential E-field across the open top. A wide range of amplitude control is available by adjusting the relative height of the bases on each side of the fin. Reversing the asymmetry reverses the field, causing a 180° phase shift at the aperture.

One of the advantages of the trough guide is the ready availability of power monitoring. Using short probes mounted at the points of high guide-E-field along the side wall and small loops along the base where H-field is strongest, these field quantities can be measured. Knowledge of both components is essential to avoid standing-wave ambiguities caused by reflections. With knowledge of the power as a function of distance within the guide, the radiated power between any two points is available. Since reflections are already taken into account with this monitoring, the measured radiated power is the actual power entering the exposed tissue.

DISCLOSURE OF THE INVENTION

The present invention relates, in general, to improvements in coupling the electromagnetic energy from an EM applicator to tissue for hyperthermia applications. More specifically, the invention relates to a method and apparatus for impedance matching of an EM applicator of the troughguide type, to efficiently couple EM energy from the applicator to lossy, high dielectric constant tissue, by means of an impedance matching or transforming layer.

In one embodiment, an impedance matching layer is comprised of a high thermal conductivity, low electrical conductivity material, i.e., boron nitride having a dielectric constant in the range of 2 to 3. Optimally sized metallic or dielectric material spheres, rods, or discs, are embedded in the material to artificially simulate an impedance matching layer of appropriate dielectric constant and thickness.

In a further embodiment, electronically tuneable artificial dielectric impedance matching regions are provided to facilitate delivery of EM hyperthermia to tissue, either singly, or in combination with US radiation.

Electronic tuning of "artificial-dielectric" regions by means of bias voltages may be used to control electrical impedance matching conditions at the interface between biological tissue and the electromagnetic applicator. Since no mechanical adjustments are required, the speed of response is high. Electronic feedback control (with or without computer intervention) is therefore possible. In addition, the matching layers can be designed so that the discrete control elements also provide monitoring information concerning the electromagnetic fields passing through them.

In yet another embodiment, diodes in a trough guide type applicator are used to cause the applicator to couple electromagnetic power from non-radiating to radiating modes in a highly controlled manner.

The new approach is also highly compatible with the shared aperture requirements of hybrid electromagnetic/ultrasound systems, as will be shown in further embodiments.

BEST MODE OF CARRYING OUT THE INVENTION

I. Artificial Dielectric Non-Tuneable Impedance Matching Layer Embodiment

Figure 1:
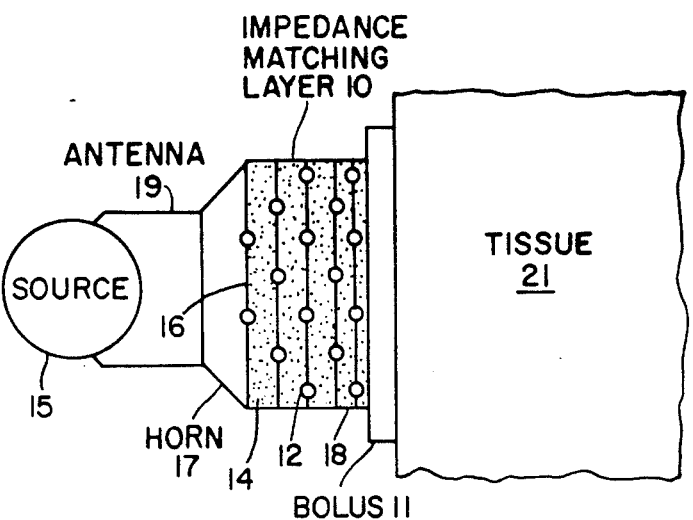
FIG. 1 is a schematic of a hyperthermia system employing an artificially created impedance matching layer 10 of the invention.

The object of the invention shown in FIG. 1 is to efficiently couple radio frequency or microwave energy generated at source 15 to lossy, high dielectric constant body tissue 21, such as the tissue found in a human body. The tissue 21 is surrounded by a bolus 11 of, for example, water for localized cooling. The source 15 is coupled to an antenna 19, such as an unloaded troughguide applicator with a horn 17. In accordance with the invention, an artificial dielectric impedance matching layer 10 is provided between the antenna 19 and the bolus 11 to efficiently couple the energy from the horn 17 to the tissue 21.

The dielectric constant for muscle tissue at 915 MHz is about 51.0. A one-quarter wavelength layer with dielectric constant of about 7.1 will approximately match the tissue impedance to that of air, assuming no loss in the tissue. At 915 MHz, this corresponds to a layer thickness of about 3.1 cm.

The thickness of the matching layer 10 depends to a limited extent on the conductivity of the tissue, and on the incident angle of wave propagation, as well as on its dielectric constant. Since leaky-wave antennas always radiate at a non-zero angle to broadside, this incident angle must be considered. Once the wave has reached the tissue, the transmitted angle is, by Snell's Law, an order of magnitude smaller than that at the troughguide aperture. If the aperture angle is 30°, the resulting angle into muscle tissue at 915 MHz is about 4°, and the layer thickness 3.2 cm.

Ideally, the matching layer 10 should be electrically as loss-less as possible to minimize power dissipation in this region. Dry table salt, which has very little conductivity and a dielectric constant of about 5.9 at 915 MHz, was used initially. Experimental results with salt showed good matching performance despite a 15% deviation from the desired value.

Two problems with using salt are that it must be kept dry so that its conductivity stays low, and that it is a poor thermal conductor. It would be preferable to employ a matching material that has a dielectric constant closer to 7.1, negligible electrical conductivity, high thermal conductivity, and relative insensitivity to water.

Figure 16:
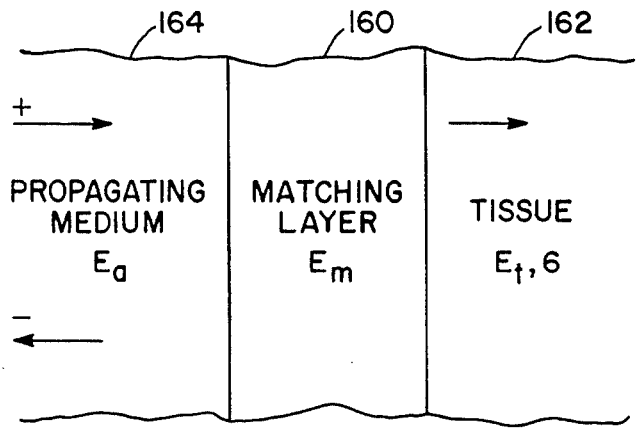
FIG. 16 is a sketch of a matching layer intermediate a propagating medium and tissue illustrating the impedance matching problem.

The problem, as illustrated in FIG. 16, is to devise an appropriate matching layer structure 160 to couple incident wave energy (+ arrow) from a propagating medium 164 having a constant $\epsilon_a$ into tissue 162 having a permittivity $\epsilon_t$. Optimally, it is required that there be no reflection of the + wave (normally incident at frequency $\omega$). Proper values of $\epsilon_m$ (permittivity of the layer 160) and length $l$ of matching layer 160 will give the desired result and can be expressed in terms of $\epsilon_a/\epsilon_o$ and $\epsilon_t/\epsilon_o$ (the dielectric constants on the applicator and tissue sides) and $\sigma$ the conductivity of the tissue.

$\epsilon_m$ and $l$ must satisfy the complex equation:

$$\frac{\sqrt{\frac{\epsilon_m}{\epsilon_a}} - 1}{\sqrt{\frac{\epsilon_m}{\epsilon_a}} + 1} e^{j(2\xi_m l)} = \frac{\sqrt{\frac{\epsilon_m}{\left(\epsilon_t - j\frac{\sigma}{\omega}\right)}} - 1}{\sqrt{\frac{\epsilon_m}{\left(\epsilon_t - j\frac{\sigma}{\omega}\right)}} + 1} \quad \text{(I)}$$

where $$\xi_m = \omega \sqrt{\mu_o \epsilon_m}$$

If $\sigma = 0$ (no loss), the well known solution is:

$$\epsilon_m = \sqrt{\epsilon_a \epsilon_t}$$

$$l = \frac{\lambda}{4} \left(\text{or odd multiple of } \frac{\lambda}{4}\right)$$

$$\lambda = \frac{2\pi}{\xi_m} = \frac{2\pi}{\omega} \sqrt{\frac{1}{\mu_o \epsilon_m}} = \frac{\sigma}{f}$$

$$= \frac{2\pi}{\omega} \cdot \frac{1}{\sqrt{\mu_o \sqrt{\epsilon_a \epsilon_t}}}$$

If $\sigma > 0$, both $\epsilon_m$ and $l$ are altered.
Notice that when $\sigma = 0$, $$\epsilon_m \sim \sqrt{\epsilon_t}$$

$$l \sim \frac{1}{\sqrt{\sqrt{\epsilon_t}}} = \epsilon_t^{\frac{1}{4}}$$

Thus $\epsilon_m$ is more sensitive to a change in $\epsilon_t$ than $l$ is.

In order to promote cooling of tissue surface, high thermal conductivity is desired. Most low loss dielectrics have low thermal conductivity. Boron nitride (BN) is an exception.

However, $\epsilon_m/\epsilon_o$ values required (when $\epsilon_a/\epsilon_o = 1$ and $\epsilon_t/\epsilon_o \sim 50-100$) are on the order of 5-10, whereas BN has $\epsilon_m/\epsilon_o \sim 2-3$.

The inventive solution to this dilemma is to synthesize an artificial dielectric with either:

(i) metallic objects (described in this Section I), or (ii) reverse-biased diodes (described in Section II) embedded in BN matrix to raise $\epsilon_m/\epsilon_o$ from 2-3 to the required value. In either case, $l$ is adjusted to a correct value which depends upon ($\epsilon_m/\epsilon_o$).

If $\epsilon_t$ and/or $\sigma$ change (different tissue characteristic), both $\epsilon_m$ and $l$ must change for perfect match. However, since $l$ is less sensitive to a change in $\epsilon_t$, a change in $\epsilon_m$ is dominant.

For example, when $\sigma = 0$:

If perfect match exists and then $\epsilon_t$ is changed by 10%, $\epsilon_m$ needs to be changed by ~5% and $l$ by 2.5%.

Therefore, an adjustment of $\epsilon_m$ and no change in $l$ will still give a reasonable (but not perfect match).

Note that greater flexibility is present in the Section II case, because the diodes can have non identical voltage bias applied to each layer, such that $V_1 \neq V_2 \neq V_3$.

Figure 17:
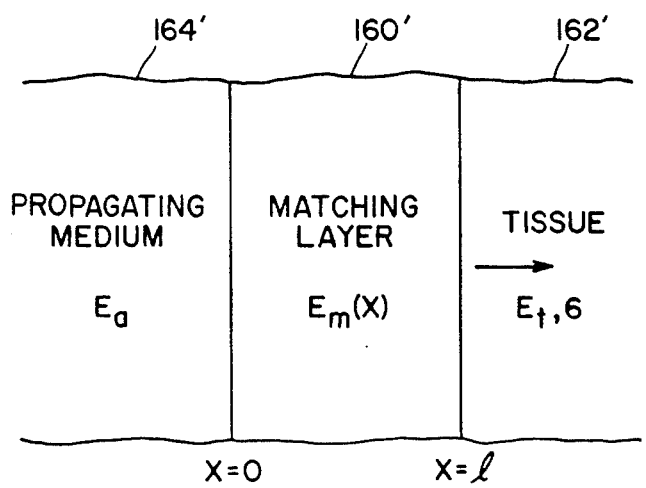
FIG. 17 is a further illustration of the matching layer problem.

This means the effective dielectric constant $\epsilon_m$ can be made a controlled function of x, $\epsilon_m(x)$. When $\epsilon_m \epsilon_m(x)$ is a gradual function. Equation I is approximately altered to:

$$\frac{\sqrt{\frac{\epsilon_m(o)}{\epsilon_a} - 1}}{\sqrt{\frac{\epsilon_m(o)}{\epsilon_a} + 1}} e^{j2\omega \sqrt{\mu_o}} \int_0^l \sqrt{\epsilon_m(x)} \, dx \approx \quad \text{(II)}$$

$$\frac{\sqrt{\frac{\epsilon_m(1)}{\epsilon_t - j\frac{\sigma}{\omega}}} - 1}{\sqrt{\frac{\epsilon_m(1)}{\epsilon_t - j\frac{\sigma}{\omega}}} + 1} \quad 5$$

as illustrated by FIG. 17.

Equation (II) can be satisfied for fixed l, by adjusting $\epsilon_m(x)$ (for diode artificial dielectric by means of voltages). In this example, all diodes in the same y-z plane have same bias, but adjacent planes can have different voltages.

A naturally occurring substance that meets the above criteria of high thermal conductivity and low electrical loss has not been identified. Instead, we have simulated such a dielectric by utilizing two or more materials having different dielectric constants, but in which the average of the two constants produces an average dielectric constant close to that of the tissue being matched. At the same time, one of the materials is selected to have good thermal conductive properties to dissipate heat generated during hyperthermy. One such simulation comprises loading a substantially electrically lossless high thermal conductivity material with conducting metal spheres, as illustrated in FIG. 1. A cubic lattice 10 of optimally sized steel ball bearings 12 surrounded by boron nitride 14, for example, in powder form, produces the desired bulk dielectric characteristics. The spheres 12 act as dipoles, concentrating the electric field and multiplying the dielectric constant of the boron nitride. Boron nitride is practically lossless, yet has high thermal conductivity. This type of matching layer dissipates no power, yet can provide for considerable surface cooling. With a dielectric constant for boron nitride powder of about 2.1, the diameter and center separation of the ball bearings are chosen to be 1.02 and 1.27 cm, respectively, to produce an effective dielectric constant multiplier of 3.3. This results in an artificial dielectric constant of 2.1×3.3 or about 7.0. The ball bearings may be affixed to thin BAKELITE® sheets 16 and held in place by a PLEXIGLASS® frame 18. The powdered boron nitride 14 is packed between bearings 12 and sheets 16. Discs, rods and other objects made of metal and/or dielectric material may be used in place of the metal spheres. The optimum size and spacing between objects represents a trade off between competing requirements of power handling capacity and power loss. If "a" is the spacing between objects and "r" is the radius of the object, it is preferable that both a and r be much smaller than the wavelength of the source.

Figure 2:
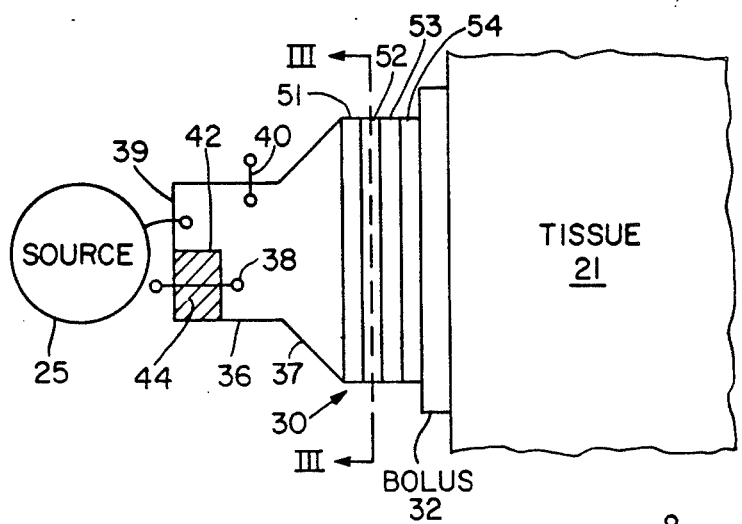
FIG. 2 is a schematic illustration of a hyperthermia system employing a voltage controlled artificial dielectric impedance matching layer embodiment of the invention.

II. Voltage-Controlled Artificial-Dielectric Impedance Matching Layer Embodiments Referring now to FIG. 2, there is shown, schematically, an alternate embodiment of the hyperthermia system utilizing a voltage controllable artificial dielectric impedance matching layer 30 of the invention. The layer 30 is disposed between a trough guide EM applicator 36 and an E field smoothing bolus 32. Bolus layer 32 may, for example, comprise a bag filled with pure water, or other dielectric, with a dielectric constant close to that of the tissue 21.

Real tissue 21 is not uniform and cylindrical, and is often difficult to contact directly. Consequently, the bolus 32 is used as an intermediary. The bolus 32 also can be used to cool the tissue surface. The power deposited in the bolus can greatly exceed that of the tissue, as long as this heat is removed and the power near the tissue surface is minimized by the bolus.

Unfortunately, due to layers of different tissue near the body surface, a bolus can never exactly match to interior muscle tissue. Also, it is preferable to minimize the bolus thickness for several reasons. For a thinner layer, waves have less of a chance to spread, and diffraction and reflection effects are smaller. Further, the cancelling of fields between adjacent unequally-phased array elements is most prominent nearest the applicator. This is a benefit near the tissue surface that should not be entirely wasted in the bolus.

Source 25 generates RF or microwave energy, which is coupled to antenna 36. Antenna 36, preferably, may comprise an asymmetric troughguide applicator of the type previously described. Antenna 36 consists of a U-shaped channel with a side opening and a horizontal center fin 42 extending from a base 39 and running the length of the guide. The base blocks 44 on one side of the fin are elevated, introducing asymmetry which produces a tangential E-field across the open side. The open side extends to a radiating horn 37 which is coupled to impedance matching layer 30. H-field loops 38 and E-field loops 40 are provided for monitoring power within the troughguide.

Figure 3:
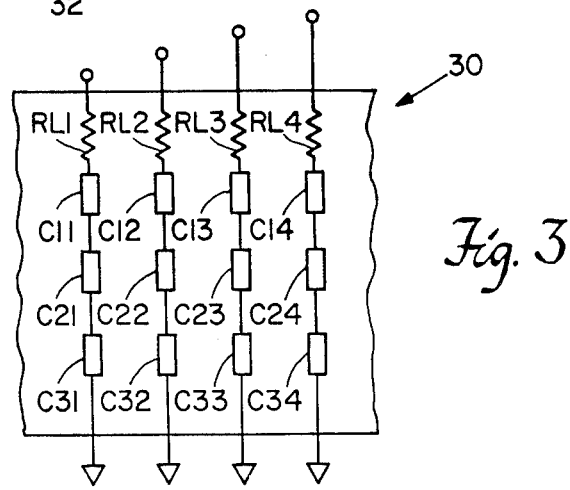
FIG. 3 is a schematic of a planar view of one level, or sheet, of the artificial impedance matching layer taken along lines III—III of FIG. 2.

Impedance matching layer 30 is comprised of a series of layered sheets. A portion of one such sheet is shown in FIG. 3 in plan view. Each sheet is comprised of an array of electronic circuits C11-C34, arranged in columns (or strings) and rows. Each column is fed a bias voltage through a respective load resistor RL1-RL4. Each column is therefore connected in series between a voltage source and ground. Using integrated circuit technology, each sheet can be formed into a thin flexible substrate layer of non-lossy dielectric material, such as polyimide.

Figure 4:
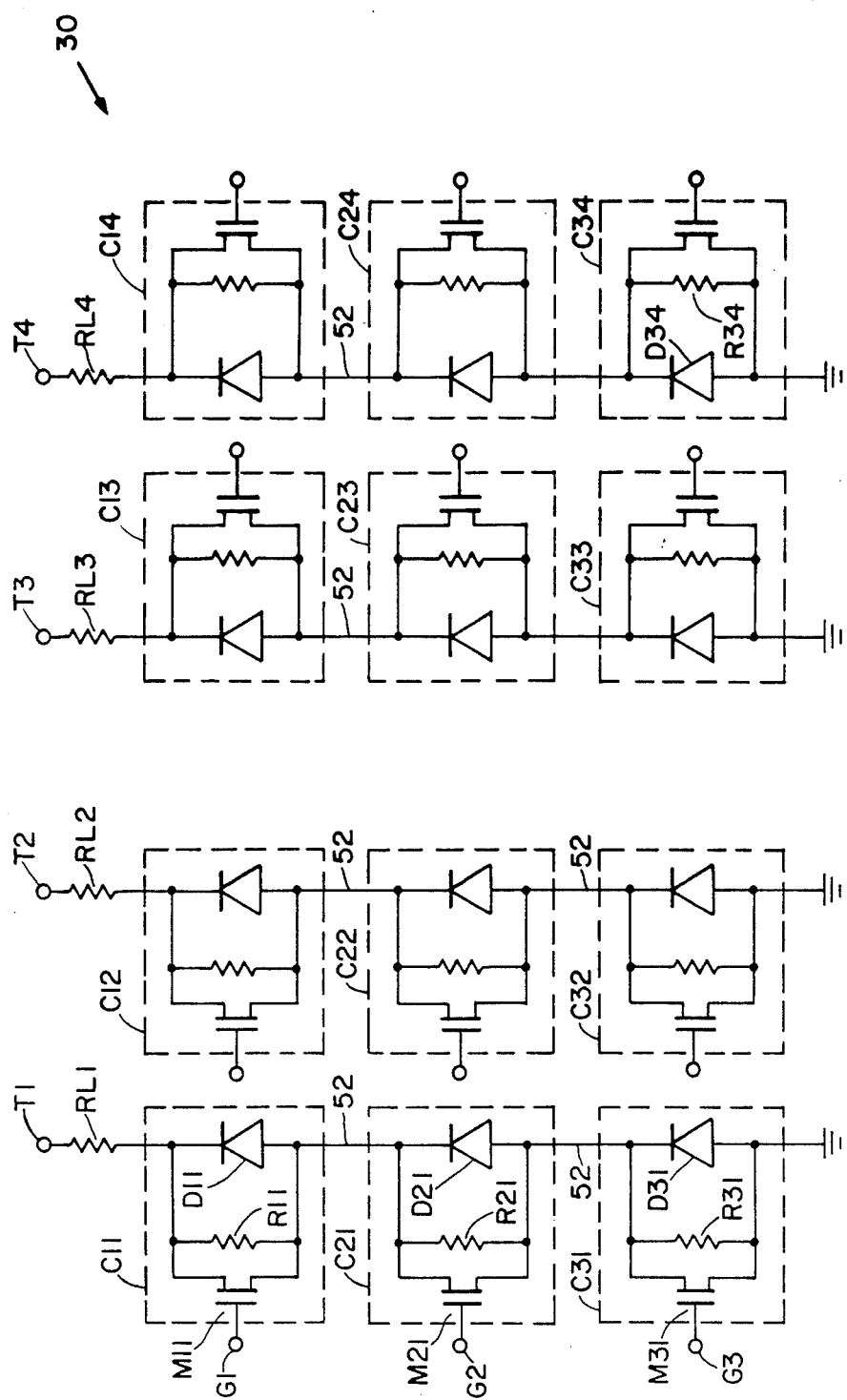
FIG. 4 is an electrical schematic of the sheet shown in FIG. 3.

As shown in more detail in FIG. 4, each column or chain, consists of a plurality of reverse biased diodes, such as D11, D21, D31, coupled in series by leads 52.

The leads 52 act as antennas, causing the voltage from the EM-field generated by source 25 to be concentrated across the junction capacitance ($C_j$) of the individual diodes. The leads 52 also permit the DC reverse voltage bias at the input terminals T1-T4 to be applied to the varactor-diodes D11, D21 and D31.

The diodes are spaced apart by a distance "a", which is much less than the wavelength λ of the EM radiation from source 25. An equivalent transmission-line with inductance per unit length $L' \simeq \mu_o$ and capacitance per unit length $$C' \simeq \epsilon_o + \frac{C_j}{a}$$

is thus formed; wherein $\mu_o = 4\pi \times 10^{-7}$ Hz/meter (permeability of free space) and $$\epsilon_o = \epsilon_o \simeq \frac{1}{36\pi} \times 10^{-9} \text{ Fds/m (permittivity of free space)}.$$

The effective constant is thus:

$$(\epsilon/\epsilon_o)_{eff} \simeq 1 + \frac{C_j}{a}$$

As a specific example, for an abrupt p-n junction, the incremental or linearized capacitance $$C_j \sim \frac{1}{\sqrt{V_{dc}}}$$

where $V_{dc}$ is the magnitude of the reverse junction bias. Therefore, the dielectric constant of the matching layer is voltage-controllable by the DC bias applied at terminals T1–T4.

In order to better equalize the dc bias voltages, resistors R11, R21, R31 may be added in parallel with the diodes, as shown in FIG. 4. The value of these resistors should be much greater than $1/\omega C_j$. Transistors, such as MOSFETs M11, M21, M31, acting as voltage-controlled resistors, may also be coupled across the varactor-diodes D11, D21, D31, respectively. Note that other voltage controlled resistors formed of JFET's or bipolar devices may be used in place of the MOSFET's. Separate matrix addressing of bias lines (horizontal) T1–T4 and gate lines (vertical) G1–G3 is then made possible. Such biases may include RF voltage components at the frequencies $\omega_1$ and $\omega_2$ supplied by modulators 56 and 58, respectively (See FIG. 5). The combination of dc voltages, i.e.. bias $(V_{dc})$ at T1, T2 or T3; and gate bias $(V_G)_k$ may be used to control the MOSFET resistance and hence the voltage divider fraction that provides bias to one particular diode (or more likely, all of the diodes in one particular plane). Because the reverse-biased varactor diode has a nonlinear voltage-current relation, it is also possible to perform frequency mixing operations that produce modulation components across load resistor $R_L$ that are proportional to the RF component of the diode current. Thus, as shown in FIG. 5, the varactor diodes can also provide an electromagnetic radiation monitoring function that is also matrix addressable.

Figure 5:
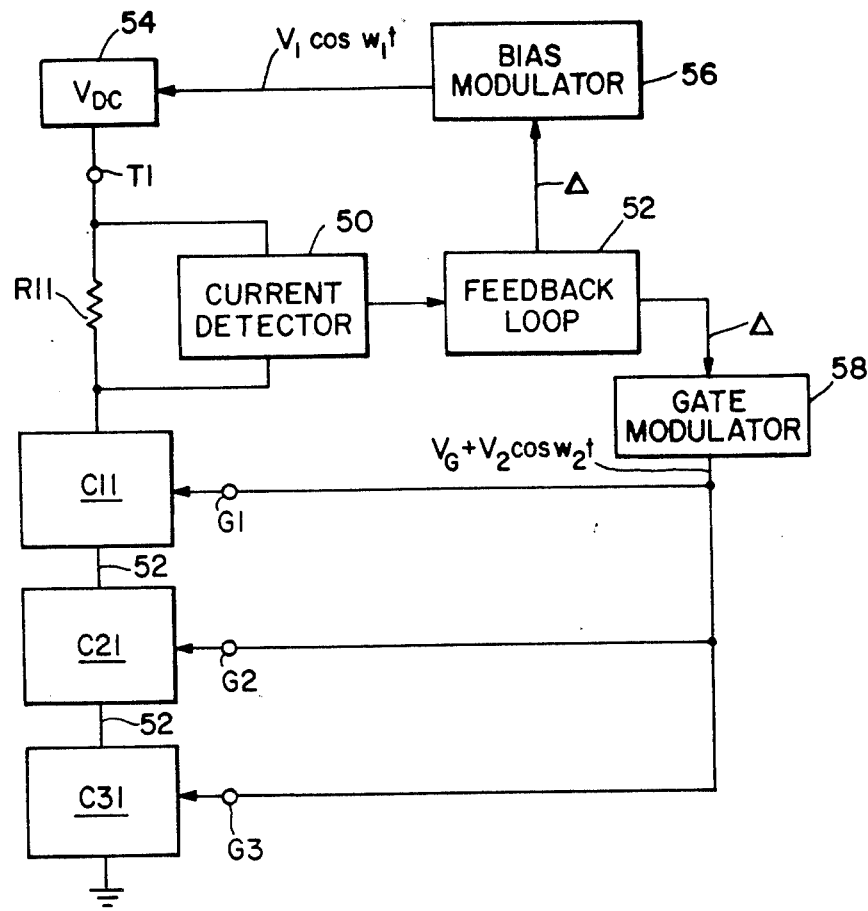
FIG. 5 is a block diagram of a circuit for monitoring and controlling the electromagnetic radiation picked up by the matching layer and for adjusting the layer accordingly.

In FIG. 5, one string of one sheet of layer 30 is depicted, schematically, showing that the DC bias voltage $V_{DC}$ may be modulated by bias modulator 56, so that the voltage applied to terminal T1 is the sum of $V_{DC}$ plus a time varying voltage $v_1 \cos \omega_1 t$. A DC gate bias source and modulator 58 also supplies a DC gate voltage $V_G$ modulated by a second frequency $\omega_2$, so that the voltage at gates G1–G3 is the sum thereof, or $V_G + v_2 \cos \omega_2 t$. The modulation at terminal T1 causes the capacitance of the diodes in circuits C11, C12, C13 to vary with time. The current through R11 is a measure of the power flowing from the source 25 through the layer 30. By sampling and measuring the current through $R_{11}$ with detector 50, the magnitude of this power can be assessed. Optionally, the sensed power value can be fed to a feed-back loop 52, compared to a reference voltage indicative of optimum power transfer and a difference signal $\Delta$ generated.

This $\Delta$ signal may then be coupled to the diode bias modulator 56 and/or the gate modulator 58 and used therein to vary the bias to optimize power transfer.

III. Varactor-Diode Control of Troughguide "Leaky-Wave" Radiation

Figure 6:
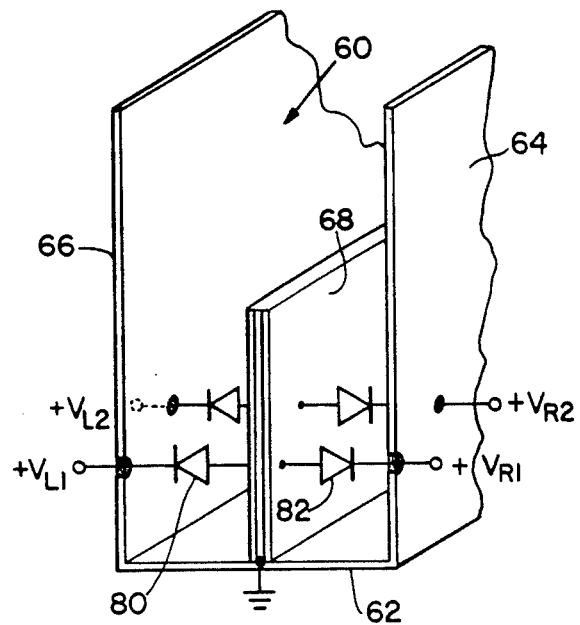
FIG. 6 is a schematic of an embodiment of the invention wherein the leaky-wave of a trough-guide applicator is generated by electronically simulated asymmetry.

In FIG. 6, an alternate embodiment is shown in which hyperthermia radiation from a symmetric troughguide 60 is controlled by varactor diodes. The guide 60, shown in partial perspective, is geometrically symmetric and consists of a U-shaped channel with a base 62; two side walls 64 and 66 and an extended center fin 68. No base blocks are utilized, such as are required in previous embodiments, to produce asymmetry. Instead, the guide is loaded periodically in the direction of propagation (into the plane of the paper) by a series of left and right reverse-biased varactor-diodes 80 and 82, respectively. If the biases are equal, so too are the junction capacitances, and no "leaky-wave" is excited. For unequal bias, the unequal capacitances are equivalent to geometrical asymmetry and "leaky-wave" radiation occurs. The direction and amount of EM generated in the guide can thus be controlled by the voltages $V_{L1}$, $V_{L2}$, $V_{R1}$, $V_{R2}$ applied across the diodes 80,82.

Figure 7:
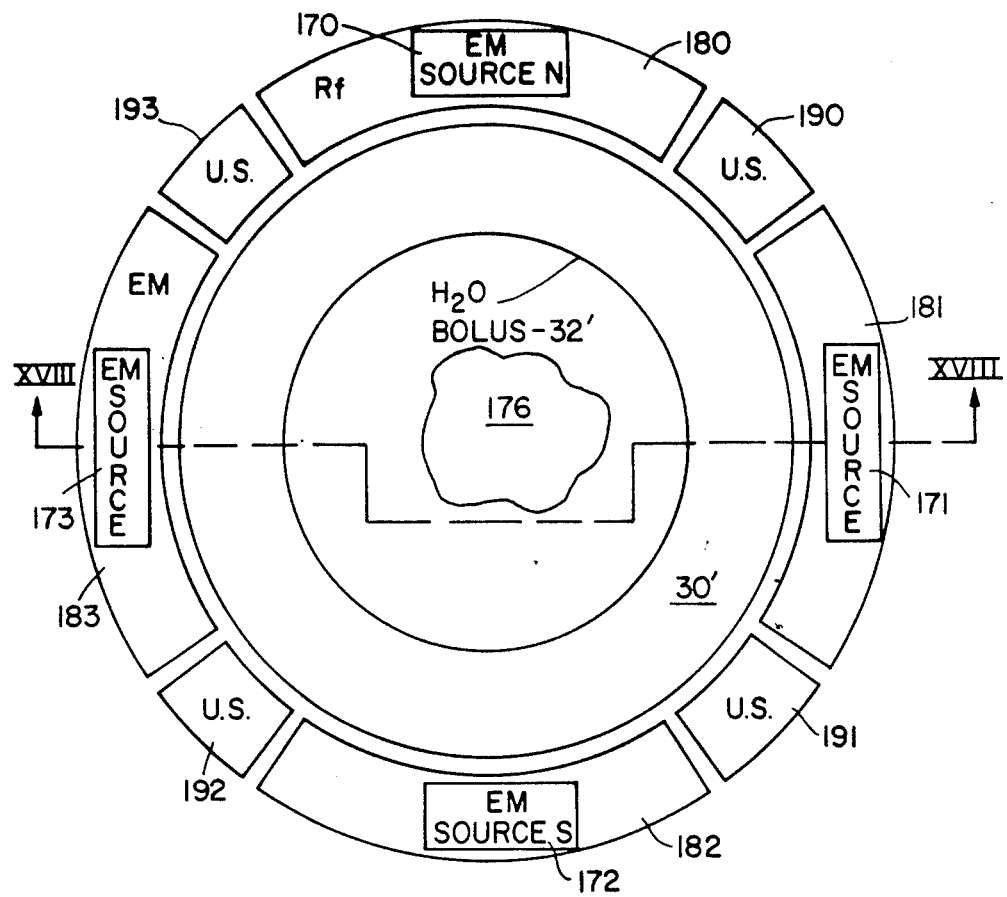
FIG. 7 is a schematic planar view of a combined electromagnetic/ultrasonic embodiment.
Figure 8:
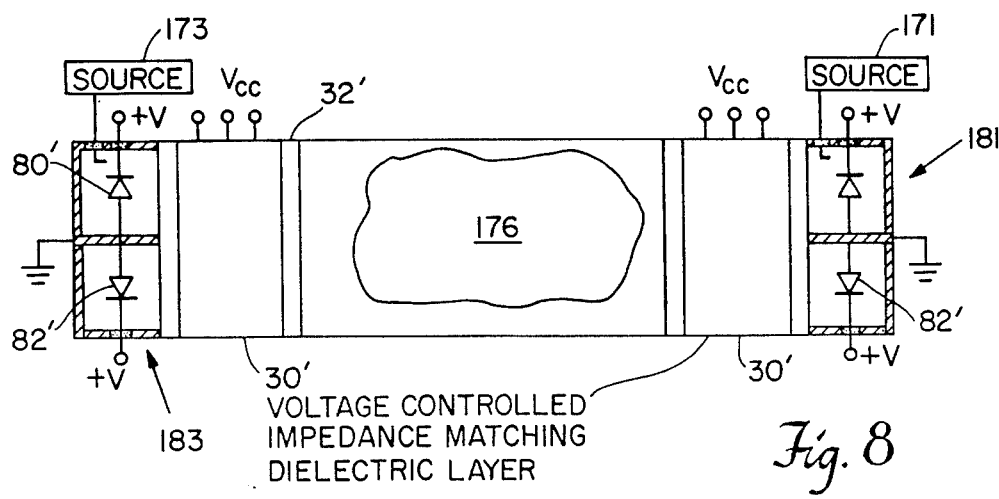
FIG. 8 is a schematic sectional view along lines XVIII—XVIII of FIG. 7.

FIGS. 7 and 8 illustrate a combined Electromagnetic-/Ultrasound Hyperthermia System that employs the above-mentioned embodiments.

In the apparatus of FIGS. 7 and 8, a body 176 may be subjected to focussing electromagnetic radiation from four radially spaced EM sources 170–173, each coupled to respective varactor controlled thoughguide leaky-wave applicators 180–183, cylindrically and symmetrically arranged about the four quadrants surrounding the body.

Four ultrasound sources 190–193 are provided with portals or apertures symmetrically arranged in gaps left between each EM applicator.

A water bolus 32' surrounds the body 176. Between the bolus and the applicators, a cylindrical array of voltage controlled diodes forms an impedance matching dielectric volume 30', of the type described in connection with FIGS. 2–5 supra.

Figure 9:
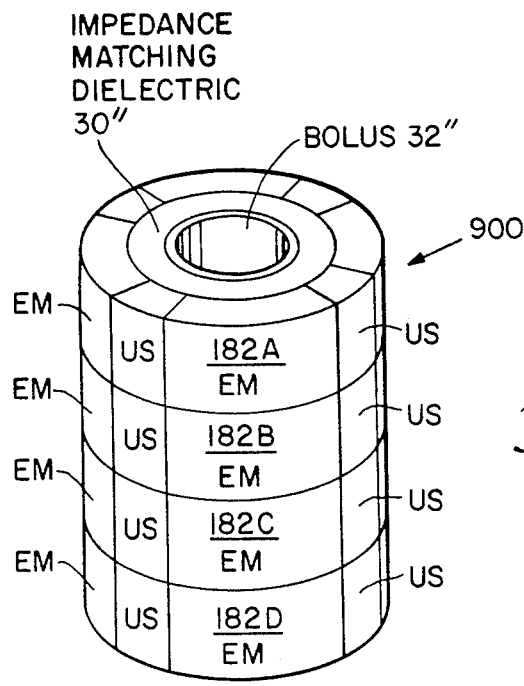
FIG. 9 is a perspective view of the individual modules of FIG. 8 stacked upon each other.

The EM applicators 180–183 are of the type previously described in connection with FIG. 6, except that the planar array of FIG. 6 is bent about an axis parallel to the tangential aperture E-field into a cylinder. Thus, each guide section 180–183 is formed into an arc of a ring. Several such sections may be stacked upon each other to form a longitudinally extended cylindrical applicator system 900, as shown in FIG. 9.

Notice that for low frequency electromagnetic frequencies, the condition $a \gg \lambda_{us}$ $a \ll \lambda_{em}$, where $\lambda_{em}$ and $\lambda_{us}$ are respectively the electromagnetic and ultrasound wave lengths. Thus, the electromagnetic aperture can be simultaneously shared by both forms of radiation without the diode array causing appreciable interference to the ultrasound.

IV. Quasi-Static Ring Array Embodiment

In non-invasive microwave hyperthermia cancer therapy, it is important to know the penetration depth limits of radiation which produces local power maxima. For treatment which provides heat at depth at the site of a localized tumor, overheating intervening tissue must be avoided. Two questions are vital to understanding the possibilities and limitations of this type of treatment: "What is the maximum radius of a sphere of biological tissue for which an optimally distributed source will generate as much power at its center as at its surface?" and "What is this optimum source distribution?"

A spherical geometry allows the greatest exposure of a focal target point to sources on the surface for a given minimum depth of lossy medium. Thus, the sphere represents the best possible non-invasive hyperthermia configuration. Although medical applications of heating spherical volumes are limited to only head and body, the knowledge gained from studying this best-case heating geometry aids in the construction of more practical hyperthermia systems.

The development of the optimal solution uses both the surface-current integration formula and the spherical harmonic solutions to the wave equation.

Figure 10:
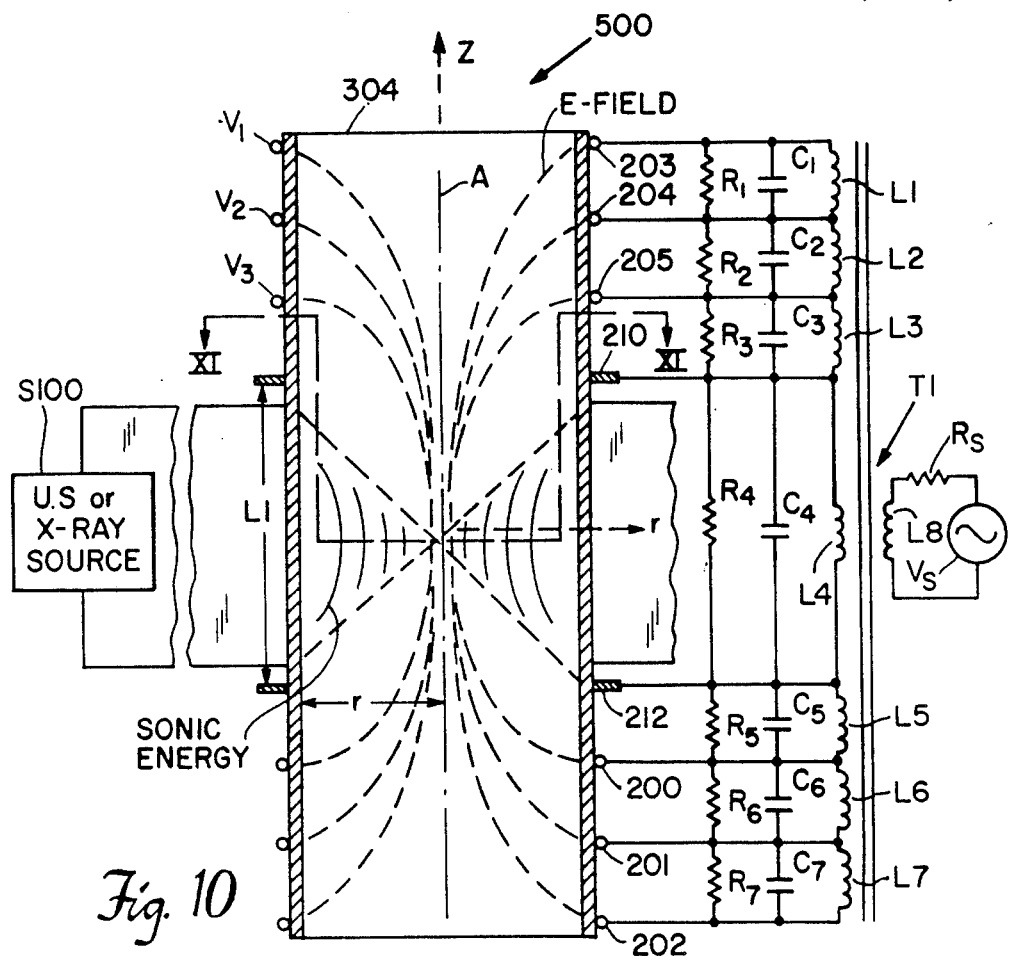
FIG. 10 is a schematic view of an alternate embodiment of the invention.

The greatest constructive interference at the center of a sphere results when the polarizations of all the surface sources are parallel: pointing in, say, the z-direction, as shown in FIG. 10. Any additional symmetrical radial component (or, correspondingly, polar-angle component) ends up cancelling itself in the center, and any unsymmetrical components perpendicular to z obviously do not contribute to the z-component.

Integrating these parallel currents on a spherical surface of radius R is straightforward for a uniform distribution $(J(r')=\delta(r-R)\hat{z}$. Without loss of generality, choose observation points along the z-axis, which lie a distance r from the sphere's center. Using the law of cosines for the source to observer distance in the Green's function integral yields:

$$E = -j\omega(I + 1/k^2 \nabla\nabla) \cdot \int_0^\pi d\theta' \int_0^{2\pi} d\phi' R^2 \sin\theta' \mu \quad (1)$$

$$\frac{e^{-jk\sqrt{R^2 + r^2 - 2rR\cos\theta'}}}{4\pi \sqrt{R^2 + r^2 - 2rR\cos\theta'}} \hat{z}$$

Figure 12:
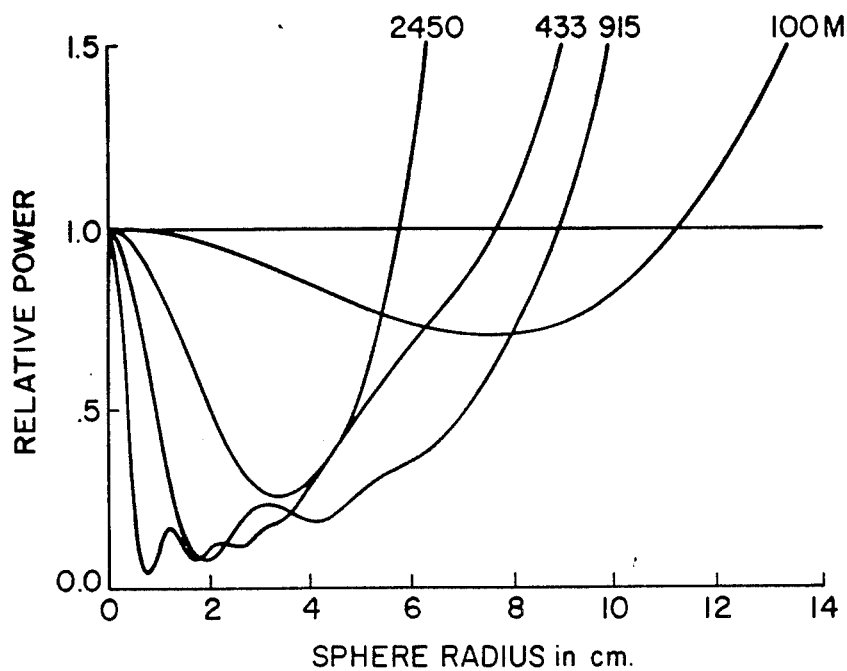
FIG. 12 is a plot of power dissipated in a sphere of muscle tissue as a function of radius for four standard hyperthermia frequencies assuming uniform current distribution.

The resulting power in a sphere of muscle tissue, normalized to that at the center, is plotted as a function of radius at $\theta = \pi/2$ in FIG. 12 for some of the important hyperthermia frequencies. For these plots, $k=\beta\cdot j\alpha$, and the values of $\alpha$ and $\beta$ were obtained for the various frequencies using experimentally derived values of dielectric constant and conductivity. Intersections of the curves with unity determine the maximum allowable radius of tissue that can be heated without overheating the surface.

Although the uniform surface current distribution intuitively seems optimal, additional improvement becomes apparent from a modal viewpoint. The harmonics of a sphere produce an electric field as represented by:

$$E = \hat{r} A_n \frac{n(n+1)}{kr} j_n(kr) P_n(\cos\theta) + \quad (2)$$

$$\hat{\theta} A_n \left[ j_{n-1}(kr) - \frac{n}{kr} j_n(kr) \right] [n\cos\theta P_n(\cos\theta) - nP_{n-1}(\cos\theta)]\left(\frac{1}{\sin\theta}\right)$$

The key feature in this equation is that since the spherical Bessel functions, $j_n$, vary as $(kr)^n$, the only mode which contributes to the electric field in the center, $r=0$, is the $n=1$ mode. The Legendre polynomials $P_0(x)$ and $P_1(x)$ evaluate to 1 and x respectively, and so it becomes evident that the first mode corresponds to the uniform surface current case. However, since the higher order modes approach 0 in the center, they can be used to counteract the large, undesirable values of field elsewhere. Specifically, a distribution can be synthesized from modes with appropriate chosen phase and amplitude to partially cancel the field at the surface and thereby increase the maximum allowable sphere size.

The distribution of power on the surface of a large, lossy sphere for uniform current varies as $\sin^2\theta$, as seen from Equation (1) with $n=1$ and be recalling $j_1(kR) << j_0(kR)$ for $kR >> 1$. Reducing the surface peak at $\pi/2$ is accomplished by adding the $n=2$ and the $n=3$ modes, which contain $\sin(3\theta)$ and $\sin(5\theta)$ terms, such that the surface power (rather than current) is more nearly a uniform function of $\theta$. With the object of minimizing the maximum surface value of the sum of modes, the coefficients $B_1$ and $B_2$ of the function $\sin(\theta) + B_2 \sin(5\theta)$ which produce 3 equal peaks are sought. An inerative method is used to find the solutions to this transcendental equation, which results in $B_1=0.2355$, $dB_2=0.0640$. Additional, higher order terms could be used, but the reduction in power would only be in the order of 0.005, not warranting the added computational complexity.

Figure 13:
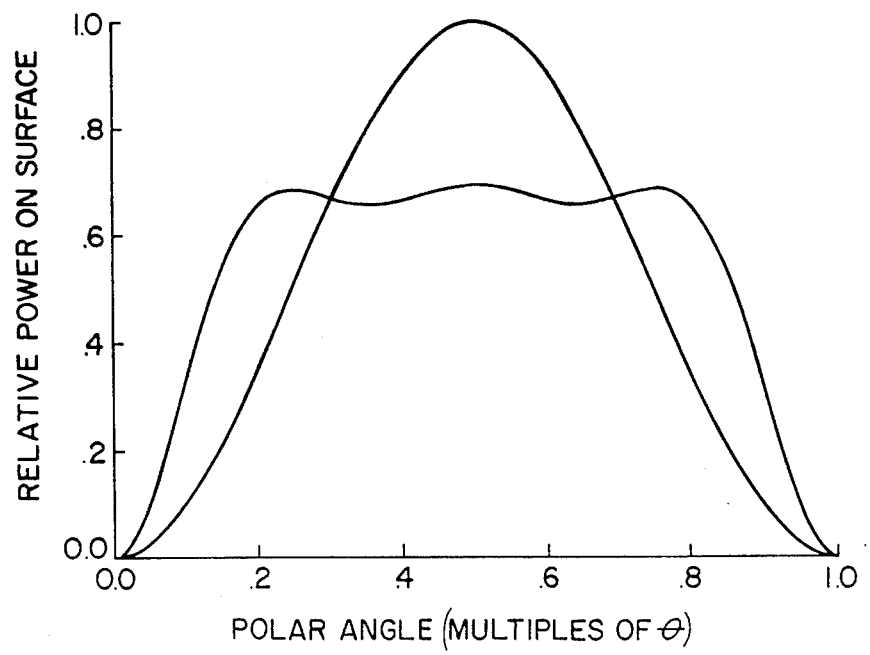
FIG. 13 is a plot of surface power as a function of polar angle for single mode (uniform current) and three mode (approximate uniform power) distributions.
Figure 14:
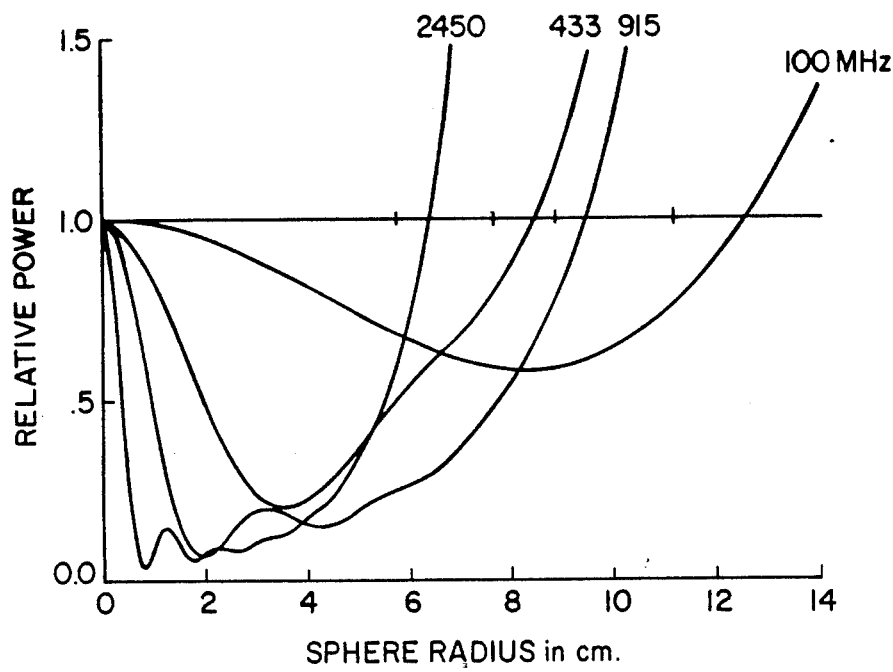
FIG. 14 is a plot of power in a sphere of muscle tissue for approximate uniform surface power distribution.

Combining the first three modes using Equation (2) with the $A_n$ chosen to compensate for the Bessel function values at R, to combine the nth-order Legendre polynomial values, and to normalize the power at the center, results in the surface power distribution shown in FIG. 13. Plotted as a function of $\theta$, it is observed that there is a sizeable reduction of peak power and that the power is more evenly spread across the surface. Also, it is clear that the fifth order ripple is very close to ideal. The normalized maximum surface power is lowered by a factor of 0.78. FIG. 14 plots the power as a function of radius at $\theta=\pi/2$ for the sum of 3 modes, for the same frequencies as in FIG. 12. Comparing these two figures shows maximum radius increases of 1.72, 0.84, 0.57, and 0.32 cm for frequencies of 100,433,915, and 2450 MHz. respectively.

Based upon the above analysis, we have determined, for the standard electromagnetic hyperthermia frequencies, the dimensions of the largest convex volume of muscle tissue which can be heated non-invasively, without overheating the surface. These limits are the theoretical best cases (within 0.5%): it is not possible to improve on them by altering the surface phase or amplitude distribution. For other tissue geometries, the maximum penetration depth will, of course, be lower.

Although penetration depth increases with decreasing frequency below 433 MHz; the resolution of the focal spot at the center decreases. However, due to the non-linear dependence of complex dielectric constant on frequency, increasing the frequency does yield an increase in penetration depth for a limited range, as shown by the plot of 915 MHz power curves. For 433 MHz, $\alpha/\beta=0.396$, whereas for 915 MHz, it is 0.231. There is a small advantage to using a more uniform power surface distribution than the uniform current distribution. The improvements are more pronounced for the lower frequencies, since wavelengths are longer, and the slopes of the power curves are shallower.

Figure 11:
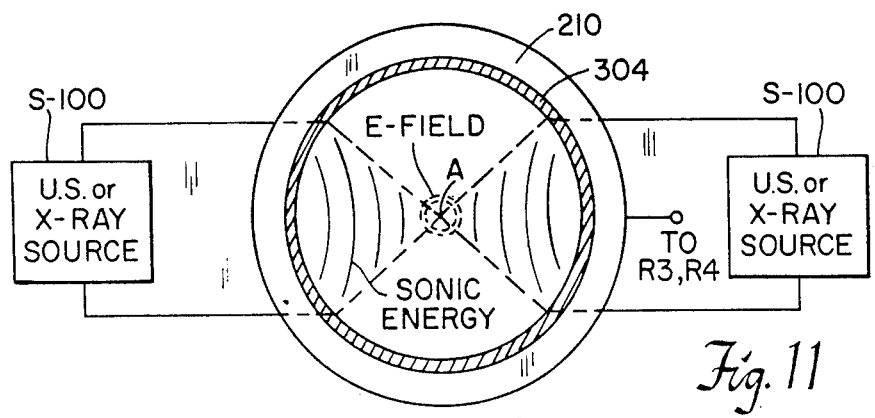
FIG. 11 is a view through lines XI—XI of FIG. 10.

FIGS. 10 and 11 illustrate an alternative embodiment of the invention utilizing the theory outlined above to construct a system wherein electromagnetic and ultrasound hyperthermia are combined with shared portals. In the apparatus of FIGS. 10 and 11. RF energy in the frequency range of about 10–100 megahertz from RF source 105 is coupled across a pair of metal electrodes 210 and 212 in the form of disc-like members affixed to a conductive cylindrical applicator 500. Rings 210 and 212 are spaced apart a distance L. Cylinder 304 has a radius r.

Figure 15:
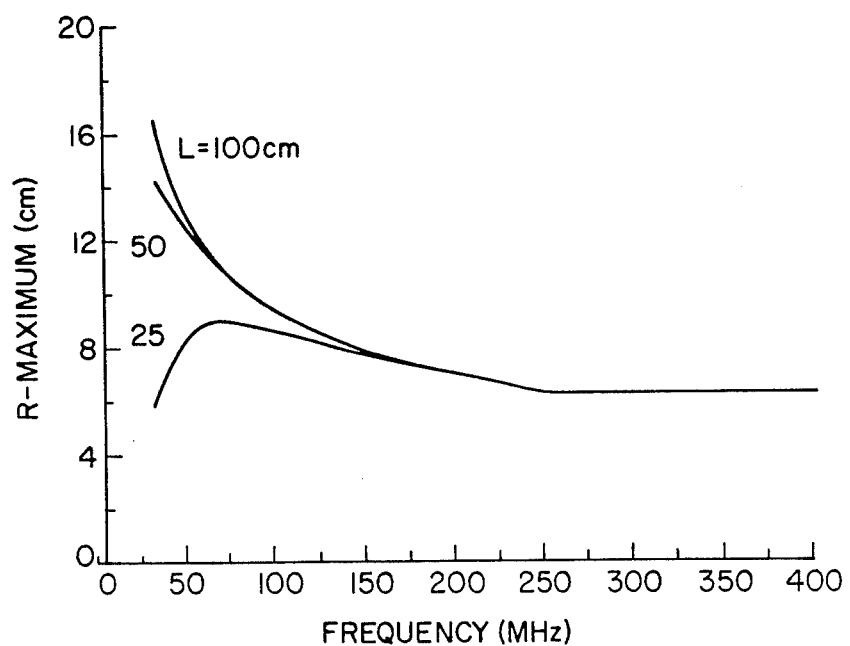
FIG. 15 is a plot of the maximum radius in centimeters as a function of frequency in hertz for a cylinder of length L at which uniform EM density in muscle tissue can be applied.

RF waves are generated about the periphery of cylinder 304 and propagate through tissue (not shown) within the cylinder. The waves interfere constructively to produce much better hyperthermia results than merely radiating from an unfocused applicator. Surrounding a volume of tissue with an RF source in this manner enables the production of localized maxima in the center. For a cylinder of given length, there is a maximum radius "R" beyond which uniform electromagnetic power density in muscle density cannot be achieved. This radius varies with frequency, as shown in the plot of FIG. 15.

In the apparatus of FIGS. 10 and 11, therefore, an RF frequency may be selected commensurate with the maximum cylinder radius R and length L, which produces the desired power density and heating on the longitudinal axis of the body tissue to be treated. Such tissue may comprise an arm or leg or a whole body which is positioned along this longitudinal axis. An optional bolus, not shown, may be provided around the body tissue similar to the system of FIG. 7. Focused sonic energy from an ultrasound or X-rays from an X-ray source, or sources, is applied to the tissue from source S100 through a portal which may extend about substantially the entire periphery of the cylinder 304 in the space L1 between rings 210 and 212.

At the same time, RF energy is applied along the longitudinal axis from RF source $V_s$. The RF energy may be distributed, as shown in FIG. 10, by coupling the RF generator $V_s$ across the primary L8 of transformer T1 connected in series with source resistor $R_s$. L8 is inductively coupled to series connected secondary windings L1–L7. Thus, RF potentials of appropriate phase and value may be coupled to parallel coupled R/C circuits R1/C1–R7/C7, and applied across the main electrodes 210/212, as well as the fringing electrodes 203–205 and 200–202. The values of these RF potentials $V_1$–$V_4$, etc. depend on the desired E-field and H-Field required in the tissue and the R and L dimensions of cylinder 304. Note that the RF energy need only be coupled at one point on each ring, leaving the remainder of the periphery of the ring available for the sonic and/or X-ray portals.

Upper fringing rings electrodes 203, 204, 205 and lower fringing rings electrodes 200, 201, 202 serve as terminating members to gradually terminate the z-directed E-field generated along the longitudinal axis by the RF energy applied across rings 210 and 212.

Ideally, the E-field should be formed axially parallel to the surface of the tissue. i.e.. in the z-direction, to avoid adverse boundary conditions and to obtain uniform heating of tissue. This condition is approached in FIG. 10 in the treatment volume extending between rings 210 and 212 and the E-field is gradually terminated in the fringing or transition region extending beyond the main ring electrodes 210 and 212 to the lower and upper fringing ring electrodes.

A computer model based upon satisfying Maxwell's equations may be used to obtain all the components of the electric field at any location within the cylinder 304 as a function of "r", the radial distance of the location from the longitudinal axis and as a function of "z" the vertical distance from the longitudinal midpoint of the cylinder. This model may be used to obtain the electric component $E_z$ (in tissue) parallel to the longitudinal axes and the electric field component $E_r$ (in tissue) transverse the longitudinal axis and the corresponding real and imaginary impedances Rr, Xr, Rz and Xz; as well as the magnetic field $H_\rho(r,z)$ in the tissue; all in cylindrical coordinates r and z. The computer program (See Appendix A) requires that the user specify the following tissue parameters: the conductivity $\sigma$ in mhos/cm and the dielectric constant K, the frequency in MHz of the power applied the radius R in cm of the cylinder and the length L in cm of the cylinder between main electrodes.

At a frequency of 50 MHz, a tissue dielectric constant of 50, a conductivity of 0.01 mhos/cm the following normalized E-field and H-Field values were obtained for various R's and L's using the program attached as Appendix A and wherein $E_o$ is the peak value of E-field at z=o and r=R.

| r/R | z/L | cm R | cm L | Real $H_\rho \cdot 120\pi/E$ | Imaginary $H_\rho \cdot 120\pi/E$ | Real $E_z/E_o$ | Imaginary $E_z/E_o$ | Real $E_r/E_o$ | Imaginary $E_r/E_o$ |
|---|---|---|---|---|---|---|---|---|---|
| 0 | 0 | 7.5 | 50 | 0 | 0 | .849 | −.524 | 0 | 0 |
| 0 | 0 | 6 | 50 | 0 | 0 | .954 | −.356 | 0 | 0 |
| 0 | 0 | 8 | 50 | 0 | 0 | .798 | −.576 | 0 | 0 |
| 0 | 0 | 10 | 50 | 0 | 0 | .534 | −.728 | 0 | 0 |
| 1 | 0 | 7.5 | 50 | 13.8 | −1.9 | 1.000 | 0 | 0 | 0 |
| 1 | .1 | 7.5 | 50 | 13.8 | −1.86 | 1.007 | 0 | .004 | .005 |
| 1 | .2 | 7.5 | 50 | 13.31 | −1.72 | .989 | 0 | .05 | −.018 |

Once the values of the E-field and H-Field in the tissue are calculated, as above, for a given tissue and cylinder assumption, the desired E-field to be provided at the air/dielectric interface $E_z(r,z)$ air, dielectric, i.e., at r=R is set equal to $E_z(R,z)$ tissue and the voltage potentials at the rings $V_1$, $V_2$, $V_3$, $V_4$ established by setting $V_1-V_2 \approx E_1 h_1$, $V_2-V_3 \approx E_2 h_2$, $E_3 h_3 \approx V_3-V_4$, etc.; wherein $E_1$, $E_2$, $E_3$, etc. is the E-field component at r=R calculated as above at z's equal to a point about half way between each set of rings and $h_1$, $h_2$, $h_3$ is the separation between ring electrodes.

Equivalents

This completes the description of the preferred embodiments of the invention. Those skilled in the art may recognize other equivalent embodiments to those described herein; which equivalents are intended to be encompassed by the claims attached hereto. For example, the disc-like electrode rings 210,212 in FIG. 10 need not be symmetric, especially in the fringing field where it may be desirable to non-uniformly distribute the E field. The ultrasound (U.S.) energy and R.F. or microwave EM energy may be synergistically combined by using the unfocussed EM energy to heat tissue to a temperature near, but below, the critical temperature of 43° C. and then using focussed U.S. to provide the precise delivery of energy to bring a focussed spot to 43° C. to destroy a tumor located at that spot.

MIT-4357 APPENDIX A

```
10 ! "E_H_Z_(r,z)"                                02/28/1987
15 !
20 !   Ez(r,z)/E(R,0)
25 !   Er(r,z)/E(R,0)
30 !   Hphi(r,z)*120pi/E(R,0)
35 !   Zr(r,z)  &  Zz(r,z)
40 !
45 !   Produced by Axial
50 !   E-Field Sources on a
55 !   Cylindrical Surface
60 !
65 !   F.R. Morgenthaler
70 !
80 DIM R(20),X(20),A$[74],B$[63],C$[39],I0Rr(5),I0Ri(5)
90 DIM I0rr(5),I0ri(5),I1rr(5),I1ri(5)
100 REAL I0Rr,I0Ri,I0rr,I0ri,I1rr,I1ri
110 P$="FF" @ CFLAG 3
120 ON KEY# 1,"PRT-O"&P$ GOSUB 220
130 ON KEY# 2," INPUT" GOSUB 250
140 ON KEY# 3,"    R" GOSUB 340
150 ON KEY# 4,"    L" GOSUB 350
160 ON KEY# 5,"  r/R" GOSUB 370
170 ON KEY# 6,"  z/L" GOSUB 390
180 ON KEY# 8,"  SOLVE" GOSUB 420
190 CLEAR
200 KEY LABEL
210 GOTO 210
220 IF FLAG(3) THEN CFLAG 3 ELSE SFLAG 3
230 IF FLAG(3) THEN P$="N" @ PRINTALL ELSE P$="FF" @ NORMAL
240 GOTO 120
250 CFLAG 1 @ CLEAR @ DISP @ DISP "f(MHz)"; @ INPUT F @ L0=30000/F
260 DISP @ DISP "K(dielectric constant)"; @ INPUT K1
270 DISP @ DISP "sigma(mhos/cm)"; @ INPUT K0 @ RETURN
280 KZ=60*L0*K0
290 U=K1-(L0/L*Z)^2 @ V=KZ
300 A=SQR((-U+SQR(U^2+V^2))/2)
310 B=SQR((U+SQR(U^2+V^2))/2)
320 A=2*PI/L0*A @ B=2*PI/L0*B
330 RETURN
340 CFLAG 1 @ CFLAG 2 @ DISP @ DISP "R(cm)"; @ INPUT R2 @ RETURN
350 CFLAG 1 @ CFLAG 2 @ DISP @ DISP "L(cm)"; @ INPUT L @ RETURN
360 RETURN
370 CFLAG 2 @ DISP @ DISP "r/R"; @ INPUT R3
380 RETURN
390 DISP @ DISP "z/L"; @ INPUT Z1
400 IF ABS(Z1)>0.75 THEN BEEP 100,100 @ GOTO 390
410 RETURN
420 IF FLAG(2) THEN 430 ELSE NORMAL @ DISP USING "2/K" ; "Please WAIT"
430 RESTORE @ U1,V1,U2,V2,U3,V3,U4,V4,U5,V5=0
440 FOR I=1 TO 5
450 READ Z,W @ GOSUB 280
460 IF FLAG(1) THEN 490
470 U=A*R2 @ V=B*R2 @ GOSUB Ik
480 I0Rr(I)=R(0) @ I0Ri(I)=X(0)
490 I0Rr=I0Rr(I) @ I0Ri=I0Ri(I)
500 IF FLAG(2) THEN 540
510 U=A*R2*R3 @ V=B*R2*R3 @ GOSUB Ik
```

```
520 I0rr(I)=R(0) @ I0ri(I)=X(0)
530 I1rr(I)=R(1) @ I1ri(I)=X(1)
540 I0rr=I0rr(I) @ I0ri=I0ri(I)
550 I1rr=I1rr(I) @ I1ri=I1ri(I)
560 C=W/0.51*COS(2*PI*Z*Z1)
570 S=W/0.51*SIN(2*PI*Z*Z1)*2*PI/L*Z
580 u1=I0rr @ v1=I0ri @ u2=I0Rr @ v2=I0Ri @ GOSUB cdiv
590 U1=U1+C*u1 @ V1=V1+C*v1
600 u1=I1rr @ v1=I1ri @ GOSUB cdiv
610 u2=A @ v2=B @ GOSUB cdiv
620 U2=U2+S*u1 @ V2=V2+S*v1
630 U3=U3+C*u1 @ V3=V3+C*v1
640 NEXT I @ SFLAG 1 @ SFLAG 2
650 u1=U3 @ v1=V3 @ u2=K0 @ v2=(1e-005/18)*F*K1 @ GOSUB cmul
660 U3=u1 @ V3=v1 @ IF R3=0 THEN 700
670 u1=U1 @ v1=V1 @ u2=U3 @ v2=V3 @ GOSUB cdiv @ U4=u1 @ V4=v1
680 u1=U2 @ v1=V2 @ GOSUB cdiv @ U5=u1 @ V5=v1
690 DATA 1.1,0.04,0.51,0.3,1.7,-0.07,0.1,0.23,2.1,0.01
700 E2=U1*U1+V1*V1+U2*U2+V2*V2 @ DISP
710 IF FLAG(3) THEN PRINTALL
720 DISP "R(cm) = ";R2,"L(cm) = ";L
730 DISP "  r/R = ";R3,"  z/L = ";Z1 @ DISP
740 DISP "!E(r,z)/Eo!^2 = ";E2 @ DISP
750 DISP "Ez_real(r,z)/Eo = ";U1
760 DISP "Ez_imag(r,z)/Eo = ";V1 @ DISP
770 DISP "Er_real(r,z)/Eo = ";U2
780 DISP "Er_imag(r,z)/Eo = ";V2 @ DISP
790 DISP "Hphi_real(r,z)*120pi/Eo = ";120*PI*U3
800 DISP "Hphi_imag(r,z)*120pi/Eo = ";120*PI*V3 @ IF R3 THEN DISP ELSE 850
810 DISP "Rr(r,z) (Ohms) = ";U4
820 DISP "Xr(r/z) (Ohms) = ";V4 @ DISP
830 DISP "Rz(r,z) (Ohms) = ";U5
840 DISP "Xz(r,z) (Ohms) = ";V5
850 RETURN
860 Ik: IF NOT U AND NOT V THEN R(0)=1 @ R(1),X(0),X(1)=0 @ RETURN
870 R(19),X(19)=1 @ R(20),X(20)=0 @ D=U*U+V*V
880 FOR K=19 TO 1 STEP -1
890 R(K-1)=R(K+1)+2*K*(U*R(K)+V*X(K))/D
900 X(K-1)=X(K+1)+2*K*(U*X(K)-V*R(K))/D
910 NEXT K
920 R,X=0
930 FOR K=1 TO 19 STEP 2
940 R=R+R(K)
950 X=X+X(K)
960 NEXT K @ D=2*(R*R+X*X)
970 U0=(FNsinh(U)*COS(V)*R+FNcosh(U)*SIN(V)*X)/D
980 V0=(FNcosh(U)*SIN(V)*R-FNsinh(U)*COS(V)*X)/D
990 FOR K=0 TO 20
1000 I1=U0*R(K)-V0*X(K)
1010 I2=U0*X(K)+V0*R(K)
1020 R(K)=I1 @ X(K)=I2
1030 NEXT K
1040 RETURN
1050 DEF FNcosh(x)
1060 E=EXP(x) @ FNcosh=0.5*(E+1/E)
1070 FNEND
1080 DEF FNsinh(x)
1090 E=EXP(x) @ FNsinh=0.5*(E-1/E)
```

```
1100 FNEND
1110 cmul: u=u1*u2-v1*v2 @ v=u1*v2+v1*u2 @ u1=u @ v1=v @ RETURN
1120 cdiv: d=u2*u2+v2*v2 @ u=u1*u2+v1*v2 @ v=v1*u2-u1*v2 @ u1=u/d @ v1=v/d @ RETURN
```

I claim:

1. A hyperthermia applicator comprising:
   (a) an electrically conductive cylinder of radius r and length l which cylinder has a longitudinal axis extending in the z direction transverse the radius r;
   (b) a pair of main electrodes disposed on the periphery of said cylinder and separated from each other by a distance L;
   (c) a source of ultrasound energy or X-ray energy;
   (d) a portal disposed between said electrodes for admitting said ultrasound or X-ray energy into the interior of said cylinder;
   (e) a source of electromagnetic energy coupled across said main electrodes;
   (f) a series of terminating electrodes disposed on the periphery of said cylinder adjacent said main electrodes;
   (g) voltage means for applying appropriate voltages to said terminating electrodes to terminate a substantially z-directed E-field generated within said cylinder between said main electrodes.

2. The applicator of claim 1 wherein the E-field is concentrated near the center of the cylinder, the frequency of the electromagnetic energy is in the range of 25 to 400 MHz, the radius of the cylinder is less than 18 centimeters, and the length of the cylinder between main electrodes is about 100 centimeters or less.

3. A method of treating a localized region of tissue, the method comprising:
   applying electromagnetic energy from a pair of main electrodes disposed about a cylinder enclosing the tissue, such that the electromagnetic energy constructively interferes to produce a localized maximum electromagnetic energy distribution along a longitudinal axis passing through the localized region of tissue to heat the tissue to a non-destructive temperature with the maximum heating occurring along said longitudinal axis; and
   applying focused energy to the localized region from an external focusable source, the energy being focused on the localized region such that destructive heating from a combination of the electromagnetic energy and the focused energy occurs primarily in the localized region.

4. The method of claim 3 wherein applying focused energy comprises applying focused ultrasound energy.

5. The method of claim 3 wherein applying focused energy comprises applying focused x-rays.

6. The method of claim 3 wherein the cylinder includes a portal through which the focused energy is directed.

7. The method of claim 6 wherein said cylinder portal is shared by the focused energy and the electromagnetic energy.

8. The method of claim 3 wherein the electromagnetic energy is applied in the form of a field directed axially parallel to the surface of the tissue.

9. The method of claim 3 wherein said electromagnetic energy is applied from a pair of ring-shaped main electrodes.

10. The method of claim 3 further comprising terminating the electromagnetic energy from said main electrodes with a pair of fringing electrodes.

11. A method of hyperthermally treating a localized region of tissue, the method comprising:
    applying electromagnetic energy from a pair of main electrodes disposed about a cylinder enclosing the tissue, such that the electromagnetic energy constructively interferes to produce a localized maximum electromagnetic energy distribution along a longitudinal axis passing through the localized region of tissue to heat the tissue to a non-destructive temperature with the maximum heating occurring along said longitudinal axis;
    terminating said electromagnetic energy on a plurality of fringing electrodes disposed about said cylinder; and
    while applying said electromagnetic energy also applying focused energy to the localized region from an external focusable source and directing the focused energy through a portal in said cylinder, the focused energy being focused on the localized region such that destructive heating from a combination of the electromagnetic energy and the focused energy occurs substantially exclusively in the localized region.

12. The method of claim 11 wherein said focused energy is ultrasound energy.

13. A hyperthermia apparatus for hyperthermally treating a localized region of tissue, comprising:
    a cylinder adapted to enclose said localized region of tissue, the cylinder having at least one portal through which focused energy is directed;
    a pair of main electrodes disposed about the cylinder and generating electromagnetic energy which passes through the tissue such that the electromagnetic energy constructively interferes to produce a localized maximum electromagnetic energy distribution along a longitudinal axis passing through the localized region of tissue to heat the tissue to a non-destructive temperature with the maximum heating occurring along said longitudinal axis;
    a plurality of fringing electrodes disposed about said cylinder for terminating the electromagnetic energy generating by said main electrodes; and
    an external focusable source applying focused energy to the localized region of tissue through said cylinder portal, the application of focused energy being such that destructive heating from a combination of the electromagnetic energy and the focused energy occurs substantially exclusively in the localized region of tissue.

14. The apparatus of claim 13 wherein the main electrodes are ring shaped and the focused energy is ultrasound energy.

* * * * *